United States Patent [19]

Krenkel

[11] Patent Number: 5,087,202
[45] Date of Patent: Feb. 11, 1992

[54] DEVICE TO FIX OR CONTROL THE MUTUAL POSITION OF TEETH

[76] Inventor: Christian Krenkel, Moosstrasse 126, A-5020 Salzburg, Austria

[21] Appl. No.: 626,296

[22] Filed: Dec. 12, 1990

[30] Foreign Application Priority Data

Dec. 27, 1989 [DE] Fed. Rep. of Germany ....... 3943098

[51] Int. Cl.⁵ .............................................. A61C 3/00
[52] U.S. Cl. ........................................ 433/215; 433/9; 433/19
[58] Field of Search ................ 433/8, 9, 18, 19, 20, 433/21, 22, 23, 215

[56] References Cited

U.S. PATENT DOCUMENTS

| 4,015,334 | 4/1977 | Moss | 433/9 |
| 4,332,563 | 6/1982 | Weissman | 433/215 |
| 4,433,960 | 2/1984 | Garito et al. | 433/215 |
| 4,904,188 | 2/1990 | Baurmash | 433/215 |

Primary Examiner—John J. Wilson
Attorney, Agent, or Firm—Wenderoth, Lind & Ponack

[57] ABSTRACT

Described is a device to fix or control the mutual position of teeth (6), comprising anchor elements each of which is to be connected by cementing to a tooth (6) and which are connected to one another by means of bars (3), where the anchor elements are designed as rings (2) or ring segments.

22 Claims, 2 Drawing Sheets

DEVICE TO FIX OR CONTROL THE MUTUAL POSITION OF TEETH

FIELD OF THE INVENTION

The invention relates to a device to fix and control the mutual position of teeth, comprising anchor elements each of which is to be connected by cementing it to a tooth and which are connected to one another by means of force transfer members.

BACKGROUND OF THE PRIOR ART

Such devices are known expecially in the form of stiff adhesive splints. They are used, for example, to stabilize teeth that have been knocked out and replanted, implanted teeth or teeth loosened due to trauma. They also serve to stabilize the teeth in the case of lower jaw fractures, the splint functioning at the same time as a traction belt, frequently in combination with traction screw osteosynthesis. Special mention deserves the possibility of using adhesive splints as place holders for premature loss of teeth or during the transition from first teeth to permanent teeth.

A plastic adhesive diluted in acrylate monomer, as marketed, for example, by Amco under the name "Super C Ortho", serves to cement the splint to the teeth. The splint can be affixed both to the outside of the teeth and (for cosmetic reasons) to their palatinal or lingual surface.

Known adhesive splints exhibit over their entire length uniform width. This leads to the adhesive splint having to be relatively wide so that the surface abutting the tooth is adequately large to be able to transfer the requisite force by means of the adhesive. Thus, the adhesive splint impedes cleaning in the region bridging the spaces between the teeth, especially since the plastic introduced as the adhesive has the tendency to spread also in the region of the spaces between the teeth.

Devices of the aforementioned kind are known not only in the form of adhesive splints resistant to bending but also in the form of anchor elements, which are connected with elastic traction members for the purposes of controlling the teeth. Here, too, a large area connection of the anchor elements to the teeth is typical, wherein the anchor elements designed as square plates can be roughened on the side facing the tooth in order to improve adhesion. In so doing, it is especially difficult to introduce the adhesive in not too large and not too small quantities.

The invention solves the problems of improving the adhesion of the anchor elements to the teeth, whereas the teeth surfaces provided with the anchor elements and the spaces between the teeth remain largely accessible. This problem is solved in that the anchor elements are designed as rings or ring segments.

The adhesive is located in the center of the ring or ring segment at the ideal adhering point and does not flow without more effort outwardly away. The adhesive surface is enlarged, the ring itself can be rather thin, since it corresponds statically to the outer reinforcement in concrete following jacketing with adhesive. The adhesion of the plastic to the rings is further improved when said rings exhibit chamfered inner walls.

If the anchor elements are connected to an adhesive splint by means of bars resistant to bending, these anchor elements have preferably a rectangular cross section so that they can be bent in a controlled manner not only from the plane of the adhesive splint but also twisted around their longitudinal axis.

If the adhesive splint bridges a tooth gap, it is advantageous if the segments having an enlarged width are distant on the one side from a continuous bar, since in this case the bar can be guided along the gum.

The adhesive splint of the invention can be prefabricated for the usual sizes of upper and lower jaws according to the usual spacing of the teeth, and in particular both for first teeth and for permanent teeth. For first teeth that already exhibit gaps (deciduous teeth), adhesive splints can be provided in which the anchor elements are omitted in the gap area.

Of course, it is possible to prefabricate adhesive splints that do not extend from the last molar of the one side to the last molar of the other side but rather abut only one segment of the teeth.

Even if adhesive splints with different spacing between the anchor elements are kept in supply, the invention is to enable these splints being adapted individually from case to case. This is enabled by the rings and bars being deformable in the cold state with pliers. To increase the ring distance, one or more rings can be deformed into a reclining oval, wheras to reduce the distance rings are deformed into standing ovals or the bars in the splint plane are bent upward or downward in the shape of a U.

The adhesive splints of the invention can be punched out of a sheet of constant thickness, where the selected thickness of a sheet depends on which static stress on the splint is to be expected in the case of application.

As the material to manufacture the adhesive splint of the invention, titanium is recommended since it is resistant to corrosion and can be readily molded into shape with suitable pliers, a feature it retains permanently in the installed state.

Individual rings of the adhesive splint can be provided in an advantageous manner with hooks into which a rubber ring or a wire ligature can be hooked to lace together the upper and lower jaw. This option is also independent of the use of a stiff adhesive splint of interest. Thus, within the scope of the invention, individual rings, which are provided with suspension hooks, can also be connected to each tooth of the upper and lower jaw and serve to anchor a ligature, which had been attached to date in a significantly less conservative manner.

The possibility of providing annular anchor elements with hooks and to attach clamping members thereto is also interesting in orthodontics. The design of the anchor element as a ring according to the invention also makes it possible here to keep the contact surface between anchor element and tooth as small as possible and, thus, prevent damage to the surface of the tooth.

Other details of the invention are explained with reference to the drawings as follows.

DESCRIPTION OF THE PREFERRED EMBODIMENTS

The illustrated adhesive splint comprises a strip, which comprises alternatingly rings 2 and bars 3 connecting said rings. In the region of rings 2 the splint is cemented to teeth 6 in known manner.

Figure 2:
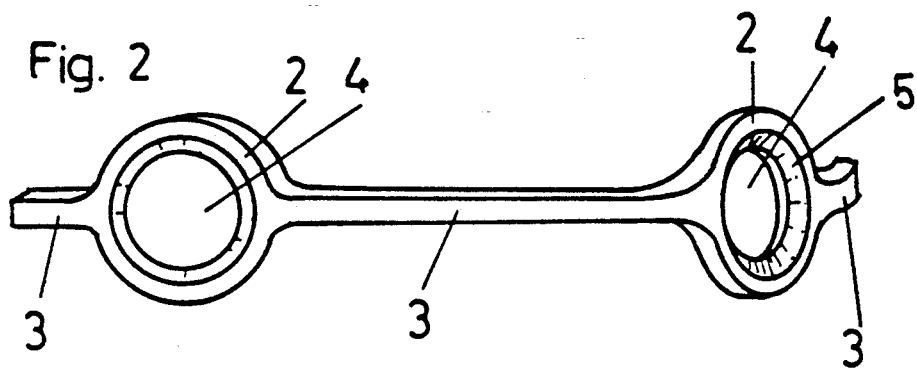
FIG. 2 is a front view of the adhesive splint.

As apparent from FIG. 2, the cementing of the rings 2 to teeth 6 is facilitated by the opening 4 of rings 2 being enclosed by chamfered walls to which the adhesive introduced into opening 4 sticks. This shape of the rings assures that the rings (possibly with the exception of their rear) are totally embedded in the plastic, where, on the one hand, the connection with the teeth is permanent and, on the other hand, the necessary bending resistance of the adhesive splint is assured.

Figure 3:
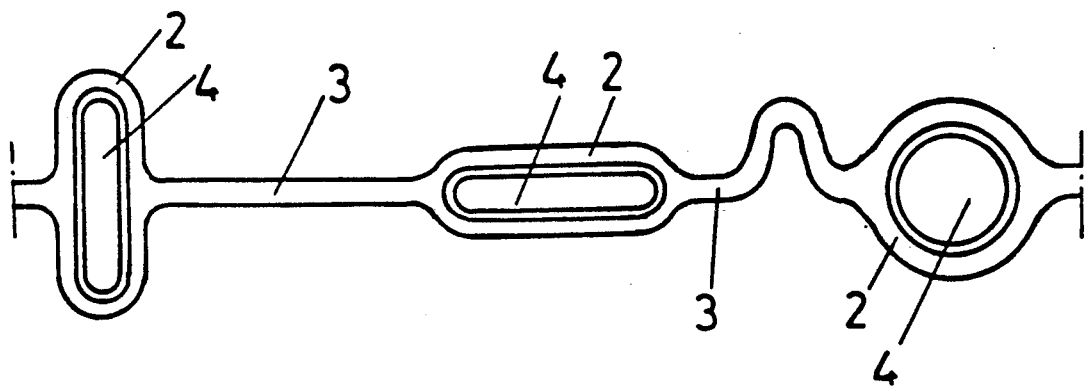
FIG. 3 shows possibilities for adapting the space of adjacent ring centers.

The adhesive splint can be adapted to the shape of the individual tooth not only by turning piece by piece around its longitudinal axis. It is also possible to change the distances between the center of openings 4 of adjacent rings 2 by changing the spacing and shapes of the rings and openings as shown indicated in FIG. 3.

Figure 1:
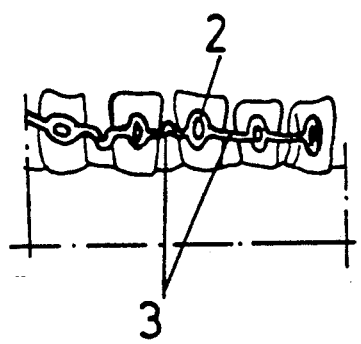
FIG. 1 shows a lower jaw with an adhesive splint attached to the teeth.
Figure 4:
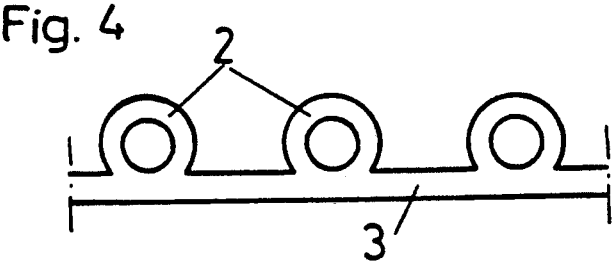
FIG. 4 is a front view of a second embodiment of the adhesive splint of the invention.

FIG. 4 shows a special shape of the adhesive splint of the invention, which is especially advantageous if gaps in the teeth are to be bridged with the adhesive splint. In the region of the gaps rings 2 are omitted, bar 3 can be guided closer to the gum than in the case of the embodiment of FIGS. 1 to 3.

Figure 5:
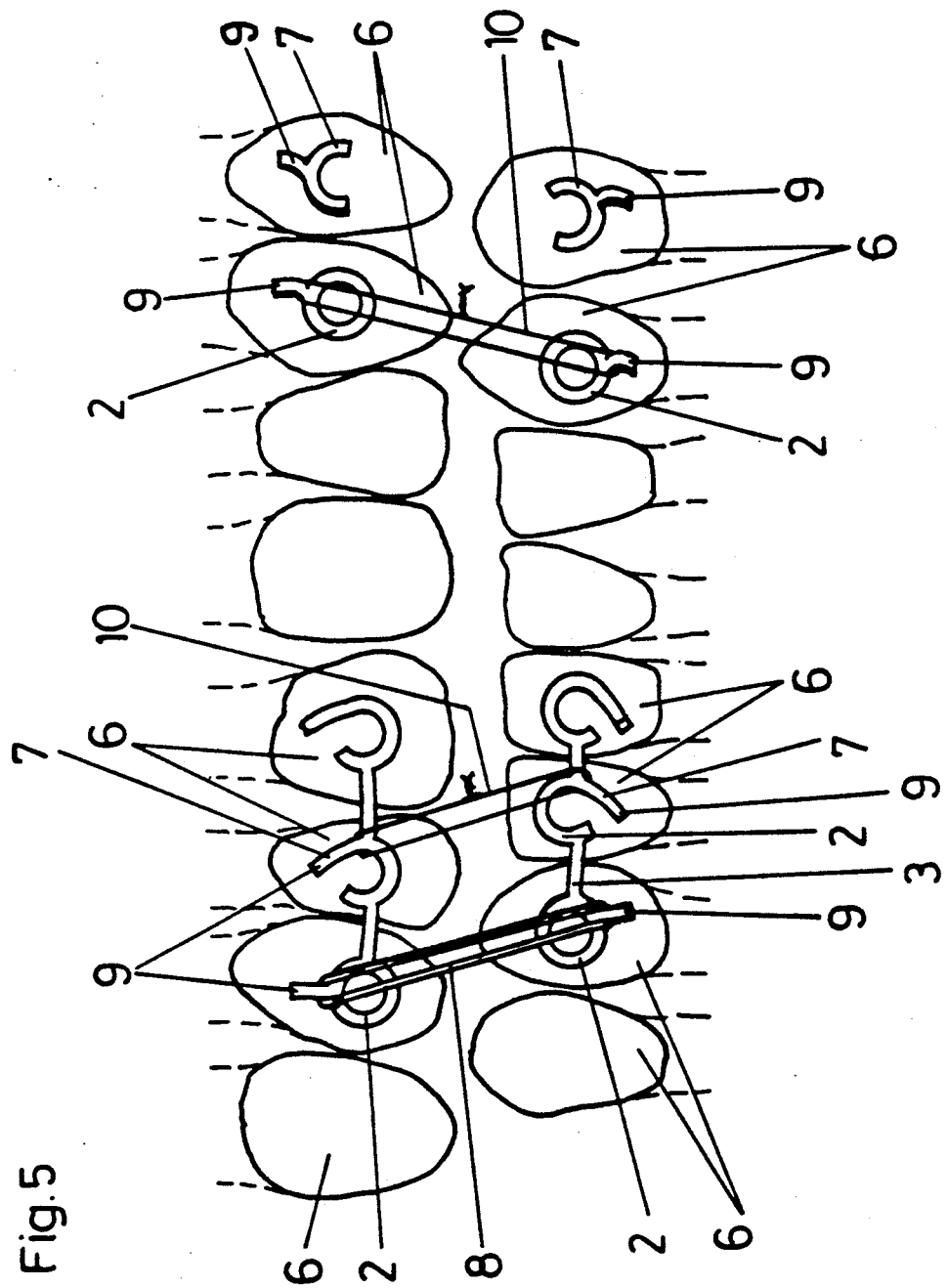
FIG. 5 shows the possibility of using the anchor elements of the invention as an attachment for ligatures to connect the upper and the lower jaw.

FIG. 5 shows, first of all, the possibility of designing the anchor elements of an adhesive splint not as rings 2 but only as ring segments 7. Even though the ring shape is statically better, one will have to be satisfied occasionally with the design as a ring segment, primarily if this design is the result of wanting to form a ring segment 7 and a hook 9 projecting from it from a closed ring 2 by pinching open. Such hooks 9 serve especially to enable the upper and lower jaw being laced together by suspending rubber rings 8 or wire ligatures 10.

To lace upper and lower jaw together, a complete bending resistant adhesive splint does not have to be provided, to this end, individual rings 2 or ring segments that are not connected by bars 3 also suffice. It is clear that such rings 2 or ring segments provided with hooks 9 are also an advantage when a horizontal force transfer between two teeth is desired for orthodontic reasons.

I claim:

1. A dental device for fixing and controlling the mutual position of teeth, comprising a flat, unitary strip of a deformable material substantially elongate in a longitudinal direction and adaptable for shaping and connection to the outer surface of teeth, said unitary strip comprising a plurality of anchor elements connected to each other by means of connecting bars, said anchor elements being substantially ring-like in configuration and having a circumference in the plane of the unitary strip, said connecting bars being substantially elongate in the longitudinal direction of the unitary strip and having a width direction in the plane of the unitary strip, wherein the circumference of said anchoring elements is substantially greater than the width of said connecting bars.

2. The dental device according to claim 1, wherein at least one anchoring element is shaped in the configuration of a closed ring.

3. The dental device according to claim 1, wherein at least one anchoring element is shaped in the configuration of an open ring.

4. The dental device according to claim 1, wherein at least one anchoring element is provided with a hook means for suspending a rubber orthodontic ring or a wire ligature.

5. The dental device according to claim 1, wherein said deformable material is a metal.

6. The dental device according to claim 1, wherein said deformable material is titanium.

7. The dental device according to claim 1, wherein said connecting bars are substantially rectangular in cross-section.

8. The dental device according to claim 1, wherein said anchor elements and connecting bars are deformable in a cold state with pliers.

9. The dental device according to claim 1, which is formed by punching out the unitary strip from a sheet of deformable material having a uniform thickness.

10. The dental device according to claim 1, wherein said anchoring elements have chamfered inner walls.

11. A dental device for fixing and controlling the mutual position of teeth, comprising a flat, unitary strip of a deformable metal substantially elongate in a longitudinal direction and adaptable for shaping and connection to the outer surface of teeth, said unitary strip comprising a plurality of anchor elements connected to each other by means of connecting bars, said anchor elements being substantially ring-like in configuration having chamfered inner walls and having a circumference in the plane of the unitary strip, said connecting bars being substantially rectangular in cross-section and elongate in the longitudinal direction of the unitary strip and having a width direction in the plane of the unitary strip, wherein the circumference of said anchoring elements is substantially greater than the width of said connecting bars.

12. A dental device for fixing and controlling the mutual position of teeth, comprising a flat, unitary strip of a deformable material substantially elongate in a longitudinal direction and adaptable for shaping and connection to the outer surface of teeth, said unitary strip comprising a continuous connecting bar and a plurality of anchor elements projecting from one side of said continuous connecting bar, said anchor elements being substantially ring-like in configuration and having a circumference in the plane of the unitary strip, said continuous connecting bar being substantially elongate in the longitudinal direction of the unitary strip and having a width direction in the plane of the unitary strip, wherein the circumference of said anchoring elements is substantially greater than the width of said continuous bar.

13. The dental device according to claim 12, wherein at least one anchoring element is shaped in the configuration of a closed ring.

14. The dental device according to claim 12, wherein at least one anchoring element is shaped in the configuration of an open ring.

15. The dental device according to claim 12, wherein at least one anchoring element is provided with a hook means for suspending a rubber orthodontic ring or a wire ligature.

16. The dental device according to claim 12, wherein said deformable material is a metal.

17. The dental device according to claim 12, wherein said deformable material is titanium.

18. The dental device according to claim 12, wherein said continuous connecting bar is substantially rectangular in cross-section.

19. The dental device according to claim 12, wherein said anchor elements and continuous connecting bar are deformable in a cold state with pliers.

20. The dental device according to claim 12, which is formed by punching out the unitary strip from a sheet of deformable material having a uniform thickness.

21. The dental device according to claim 12, wherein said anchoring elements have chamfered inner walls.

22. A dental device for fixing and controlling the mutual position of teeth, comprising a flat, unitary strip of a deformable metal substantially elongate in a longitudinal direction and adaptable for shaping and connection to the outer surface of teeth, said unitary strip comprising a continuous connecting bar and a plurality of anchor elements projecting from one side of said continuous connecting bar, said anchor elements being substantially ring-like in configuration having chamfered inner walls and having a circumference in the plane of the unitary strip, said continuous connecting bar being substantially rectangular in cross-section and elongate in the longitudinal direction of the unitary strip and having a width direction in the plane of the unitary strip, wherein the circumference of said anchoring elements is substantially greater than the width of said continuous bar.

* * * * *